United States Patent [19]

Friary

[11] Patent Number: 5,393,753
[45] Date of Patent: Feb. 28, 1995

[54] SUBSTITUTED IMIDAZOBENZAZEPINES

[75] Inventor: Richard J. Friary, West Orange, N.J.

[73] Assignee: Schering Corporation, Kenilworth, N.J.

[21] Appl. No.: 39,038

[22] PCT Filed: Oct. 4, 1991

[86] PCT No.: PCT/US91/07156

§ 371 Date: Apr. 6, 1993

§ 102(e) Date: Apr. 6, 1993

[87] PCT Pub. No.: WO92/06981

PCT Pub. Date: Apr. 30, 1992

Related U.S. Application Data

[63] Continuation of Ser. No. 595,331, Oct. 10, 1990, abandoned.

[51] Int. Cl.⁶ .................. C07D 487/04; A61K 31/55
[52] U.S. Cl. ..................... 514/214; 540/578; 540/579
[58] Field of Search ............... 540/528, 529; 514/214

[56] References Cited

U.S. PATENT DOCUMENTS

| | | | |
|---|---|---|---|
| 3,272,826 | 9/1969 | Jucker et al. | 260/293.4 |
| 3,442,903 | 5/1969 | Galantay | 260/302 |
| 3,458,522 | 7/1969 | Galantay | 260/293.4 |
| 3,485,846 | 12/1989 | Galantay | 260/293 |
| 3,491,103 | 1/1970 | Jucker | 260/293.4 |
| 3,682,930 | 8/1972 | Bourguin et al. | 424/267 |
| 3,770,728 | 11/1973 | Bourguin | 260/240 |
| 3,960,894 | 6/1976 | Bourguin | 424/267 |
| 3,994,915 | 11/1976 | Salmond | 260/307 R |
| 4,355,036 | 10/1982 | Villani | 424/267 |
| 4,596,809 | 6/1986 | Scherlock et al. | 514/293 |
| 4,609,664 | 9/1986 | Hasspacker | 514/324 |
| 4,826,853 | 5/1989 | Piwinski et al. | 514/290 |
| 5,089,496 | 2/1992 | Piwinski et al. | 514/253 |

FOREIGN PATENT DOCUMENTS

| | | |
|---|---|---|
| 0000716 | 2/1979 | European Pat. Off. . |
| 0042544 | 12/1981 | European Pat. Off. . |
| 0371805 | 6/1990 | European Pat. Off. . |
| 1371443 | 6/1964 | France . |
| 1447527 | 2/1968 | France . |
| 579077 | 8/1976 | Switzerland . |
| WO89/10363 | 11/1989 | WIPO . |
| WO89/10369 | 11/1989 | WIPO . |

OTHER PUBLICATIONS

Robey et al, J. Heterocyclic Chem., 26, pp. 779–783 (1989).
Remy et al. J. Med. Chem. (1982), 25, 231–234.
Remy et al. J. Med. chem. (1983), 26 974–980.
Galantay et al., J. Med. Chem. (1974), vol. 17, No. 12, pp. 1316–1327.
Maurer et al., Journal of Chromatography, 430 (1988) 31–41.

*Primary Examiner*—Robert T. Bond
*Assistant Examiner*—Philip I. Datlow
*Attorney, Agent, or Firm*—Henry C. Jeanette; Matthew Boxer

[57] ABSTRACT

Compounds of the formula

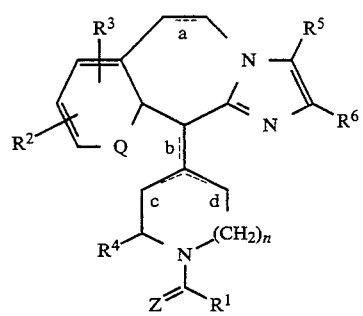

wherein $R^1$ is H, $C_1$–$C_7$ alkyl, $C_3$–$C_7$ cycloalkyl, $CF_3$, aryl, substituted aryl, heteroaryl, -O-$C_1$–$C_7$ alkyl, or -O-$C_3$–$C_7$ cycloalkyl; $R^2$ and $R^3$ are each independently H, $C_1$–$C_7$ alkyl, $C_3$–$C_7$ cycloalkyl, $CF_3$, $NO_2$, halogen, $OR^7$, $NR^8R^9$ or $S(O)_mR^{10}$, wherein m is 0, 1 or 2; $R^4$ is H, $C_1$–$C_7$ alkyl, arylmethyl, or substituted arylmethyl; $R^5$ and $R^6$ are each independently H, $C_1$–$C_7$ alkyl, $C_3$–$C_7$ cycloalkyl, aryl, substituted aryl, heteroaryl, arylmethyl, substituted arylmethyl, or taken together constitute a chain of $(CH_2)_k$ groups, wherein k is 3, 4, or (Abstract continued on next page.)

5; $R^7$, $R^8$ and $R^9$ are each independently H, $C_1$–$C_7$ alkyl, -C(=O)-($C_1$–$C_7$ alkyl), -C(=O)-aryl, or -(C=O)-heteroaryl; $R^{10}$ is $C_1$–$C_7$ alkyl, $C_3$–$C_7$ cycloalkyl, aryl, substituted aryl, heteroaryl, substituted heteroaryl, arylmethyl, or substituted arylmethyl; one and only one of the dotted lines, a, b, c, and d, represents a carbon-carbon bond; n is 0, 1, 2 or 3; Z is O or S, Q is CH, N, or NO, with the proviso that Z is not S when Q is NO, or a pharmaceutically acceptable acid addition salt thereof, are described. These compounds are useful as agents in the treatment of asthma and other allergic diseases and in the treatment of inflammation.

14 Claims, No Drawings

SUBSTITUTED IMIDAZOBENZAZEPINES

The present application is the United States national application corresponding to International Application No. PCT/US91/07156, filed Oct. 4, 1991 and designating the United States, which application is in turn a continuation of U.S. Application Ser. No. 07/595331, filed Oct. 10, 1990, and now abandoned, the benefit of which applications are claimed pursuant to the provisions of 35 U.S.C. SS 120, 363 and 365(C).

SUMMARY OF THE INVENTION

The invention relates to compounds of the formula:

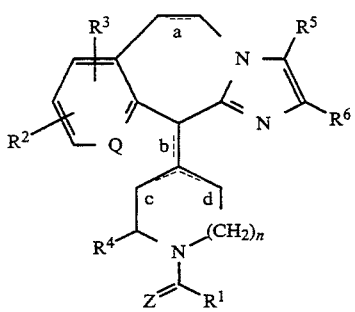

1.0 wherein $R^1$ is H, $C_1$–$C_7$ alkyl, $C_3$–$C_7$ cycloalkyl, $CF_3$, aryl, substituted aryl, heteroaryl, -O-$C_1$–$C_7$ alkyl, or -O-$C_3$–$C_7$ cycloalkyl; $R^2$ and $R^3$ are each independently H, $C_1$–$C_7$ alkyl, $C_3$–$C_7$ cycloalkyl, $CF_3$, $NO_2$, halogen, $OR^7$, $NR^8R^9$ or $S(O)_m R^{10}$, wherein m is 0, 1 or 2; $R^4$ is H, $C_1$–$C_7$ alkyl, arylmethyl, or substituted arylmethyl; $R^5$ and $R^6$ are each independently H, $C_1$–$C_7$ alkyl, $C_3$–$C_7$ cycloalkyl, aryl, substituted aryl, heteroaryl, arylmethyl, substituted arylmethyl, or taken together constitute a chain of $(CH_2)_k$ groups, wherein k is 3, 4, or 5; $R^7$, $R^8$ and $R^9$ are each independently H, $C_1$–$C_7$ alkyl, -C(=O)-($C_1$–$C_7$ alkyl), -C(=O)aryl, or -C(=O)-heteroaryl; $R^{10}$ is $C_1$–$C_7$ alkyl, $C_3$–$C_7$ cycloalkyl, aryl, substituted aryl, heteroaryl, substituted heteroaryl, arylmethyl, or substituted arylmethyl; one and only one of the dotted lines, a, b, c, and d, represents a carbon-carbon bond; n is 0, 1, 2, or 3; Z is O or S, Q is CH, N or NO, with the proviso that Z is not S when Q is NO, or pharmaceutically acceptable acid addition salts thereof.

Preferred compounds of formula 1.0 are those wherein one and only one of the dotted lines a and b is a carbon-carbon bond and Q is CH.

More preferred are compounds of formula 1.0 wherein the dotted line b represents a carbon-carbon bond; Q is CH; $R^1$ is H, $C_1$–$C_7$ alkyl or heteroaryl; $R^2$ is H or halogen; $R^3$ is H or halogen; $R^4$ is H; $R^5$ and $R^6$ are each H; and n is 1.

Of these, compounds wherein Z is O, and $R^3$ is H are even more preferred. Most preferred are compounds as described just above wherein $R^1$ is

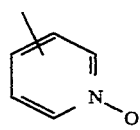

and $R^2$ is H or chlorine meta to the Q position.

Also preferred are compounds as described just above wherein $R^1$ is $C_1$–$C_7$ alkyl and $R^2$ is H or chlorine meta to the Q position.

Also preferred are compounds as described just above wherein $R^1$ is

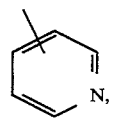

and $R^2$ is H or chlorine meta to the Q position.

Still another preferred compound of formula 1.0 is

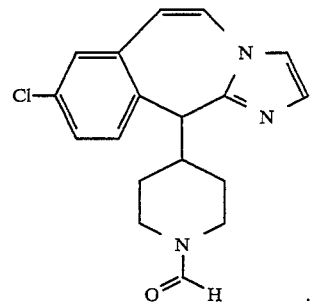

Exemplary compounds of the invention are:

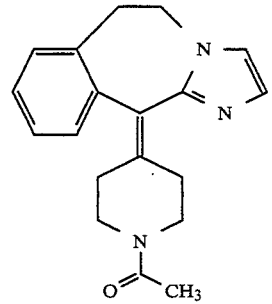

E and

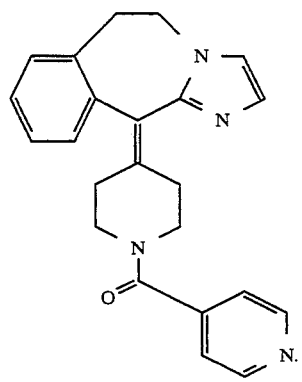

A

A most preferred compound of the invention is:

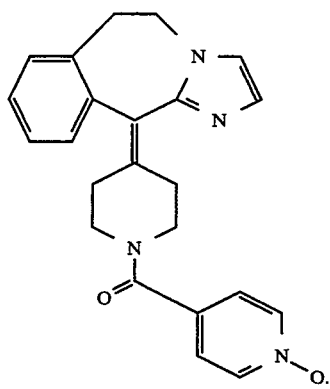

Due to their platelet activating factor(PAF)-antagonist activity, the compounds of formula 1.0 are useful in treating allergic reactions in mammals, e.g. man. In general, the compounds of formula 1.0 may be used to treat any condition in which mediation of PAF is involved, Specifically, these compounds are useful as agents for the treatment of asthma and other allergic diseases. These compounds are also useful as agents in the treatment of inflammation. In particular, these compounds are useful for the oral treatment of asthma and other allergic diseases and the oral treatment of inflammation.

The invention also relates to pharmaceutical compositions for treating allergic diseases which compose an anti-allergic, ally effective amount of a compound of formula 1.0 and an inert pharmaceutical carder material. The invention also relates to pharmaceutical compositions for treating inflammation which comprise an anti-inflammatory effective amount of a compound of formula 1.0 and an inert pharmaceutical carder material.

The invention also relates to a method for treating allergic diseases which comprises administering to a host in need of such treatment an anti-allergically effective amount of a compound of formula 1.0. The invention also relates to a method for treating inflammation which comprises administering to a host in need of such treatment an anti-inflammatory effective amount of a compound of formula 1.0.

DETAILED DESCRIPTION OF THE INVENTION

Compounds of formula 1.0 of the invention form pharmaceutically acceptable acid addition salts with any of a variety of inorganic and organic acids. Examples of suitable acids for salt formation are hydrochloric, sulfuric, phosphoric, acetic, citric, oxalic, malonic, salicylic, malic, fumaric, succinic, ascorbic, maleic, methanesulfonic and the like.

The free base forms may be regenerated by treating the salt form with a base. For example, dilute aqueous base solutions may be utilized. Dilute aqueous sodium hydroxide, potassium carbonate, ammonia and sodium bicarbonate solutions are suitable for this purpose. The free base forms differ from their respective salt forms somewhat in certain physical properties such as solubility in polar solvents, but the salts are otherwise equivalent to their respective free base forms for the purposes of this invention.

Certain compounds of the invention may exist in isomeric forms. The invention contemplates all such isomers beth in pure form and in admixture, including racemic mixtures.

As used herein the term "alkyl" denotes a straight or branched chain saturated hydrocarbon of up to 10 carbon atoms. The number of carbon atoms may be designated. For example, "$C_1$-$C_7$ alkyl" (including the alkyl portions of $C_1$-$C_7$ alkoxy, etc.)—represents a straight or branched, saturated hydrocarbon chain having from 1 to 7, carbon atoms.

"Cycloalkyl" denotes a saturated hydrocarbon ring of 3 to 10 carbon atoms. The number of carbon atoms may be designated. For example. "$C_3$-$C_7$" cycloalkyl refers to rings of 3 to 7 carbon atoms.

"Aryl" (including the aryl portion of arylmethyl, etc.)—denotes a carbocyclic group having from 6 to 14 carbon atoms and having at least one benzenoid ring with all available suitable carbon atoms of the carbocyclic group being intended as possible points of attachment.

The term "substituted aryl" (including the substituted aryl portion of substituted arylmethyl) denotes an aryl wherein 1 to 3 hydrogen atoms thereof are replaced by the same or different substituents each independently selected from the group consisting of halogen, alkyl, hydroxy, alkoxy, phenoxy, amino, alkylamino, and dialkylamino. Preferred substituents are halogen or $C_1$-$C_7$ alkyl. In particular, chlorine, methyl and ethyl are preferred substituents.

"Heteroaryl" denotes a cyclic group having at least one O, S and/or N interrupting a carbocyclic ring structure, and where the heteroatom is N, optionally including N-oxides thereof, and having a sufficient number of delocalized pi electrons to provide aromatic character, with the aromatic heterocyclic group having from 2 to 14, preferably from 2 to 10 carbon atoms. The following groups exemplify "heteroaryl", but the invention is not limited to these groups: 2-, 3- or 4-pyridyl or N-oxides thereof, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadizolyl], 2-, 3-, 4-, 5-, 6- or 7-benzofuranyl, 2-, 3-, 4-, 5-, 6- or 7-indolyl, 3-, 4- , 4- or 5-pyrazolyl, 2-, 4- or 5-oxazolyl, etc. Preferred heteroaryl groups are 2-, 3- or 4-pyridyl, or N-oxides thereof.

The term "substituted heteroaryl" denotes a heteroaryl wherein 1 to 3 hydrogen atoms bonded to carbon atoms are replaced by the same or different substituents each independently selected from the group consisting of halogen, alkyl, hydroxy, alkoxy, phenoxy, amino, alkylamino, and dialkylamino. Preferred substituents are halogen or $C_1$-$C_7$ alkyl. In particular, chlorine, methyl and ethyl are preferred substituents.

The term "halogen", which is used interchangeably with the term "halo", denotes chlorine, fluorine, bromine, and iodine.

The term "chlorine meta to the Q position" means a chlorine in the following position:

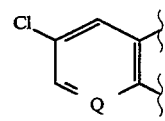

Where a line is drawn into a ring, it represents a bond at any position available for bonding on the ring. Thus

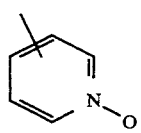

represents 2-, 3-, or 4-pyridyl N-oxides.

Compounds of formula 1.0 and intermediates thereof are prepared by processes (a) through (j) below in which $R^1$, $R^2$, $R3$, $R^4$, $R^5$, $R^6$, Q, Z, a, b, c, d and n are as above unless otherwise noted.

(a) A compound (1.1) of formula 1.0, wherein Q is CH or N-O and wherein T is C(=Z)$R^1$, or of formula 3.0, wherein T is H, is made by reacting a compound of formula 2.0. wherein Q is CH or N-O and in which T is C(=Z)$R^1$, or of formula 2.0, wherein T is H, with an acid:

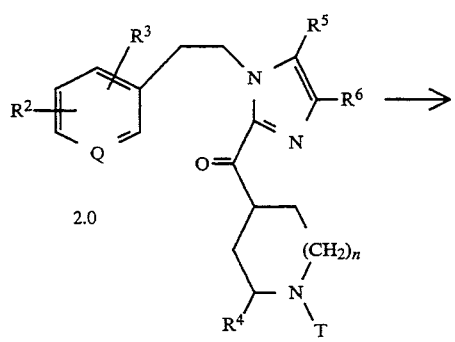

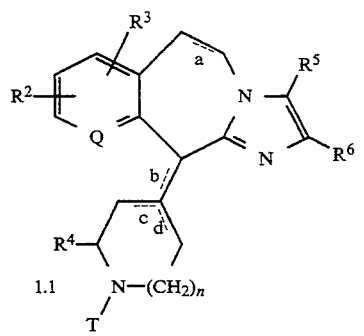

or

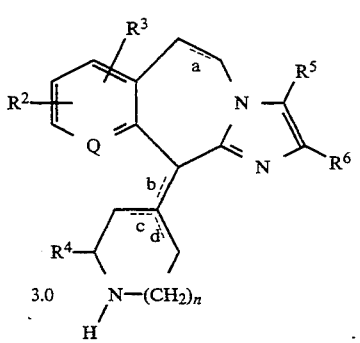

Suitable acids are mineral or strong organic acids. Mineral acids may be selected from the group consisting of concentrated sulfuric, hydrochloric, hydrobromic, hydrofluoric, and polyphosphoric acids. Strong organic acids may be selected from the group consisting of trifluoromethanesulfonic acid, methanesulfonic add, and Eaton's reagent, a mixture of methanesulfonic acid and phosphorous pentoxide. A preferred add is trifluoromethanesulfonic acid.

The reaction can be carded out at temperatures from about $-10°$ C. to $+150°$ C., and is preferably carded out at about $+25°$ C. to $+100°$ C.

(b) A compound (1.2) of formula 1.0, wherein Q is CH or N-O, is made by allowing a compound of formula 3.0, wherein Q is CH, N, or N-O, to react with an organic carboxylic add, $R^1CO_2H$, and a coupling reagent, which is described below:

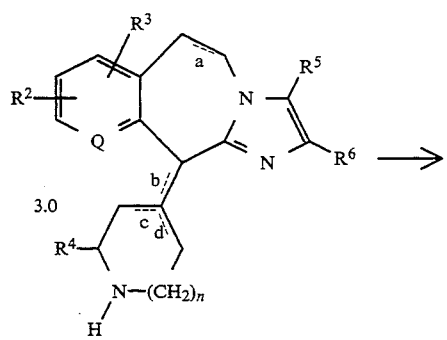

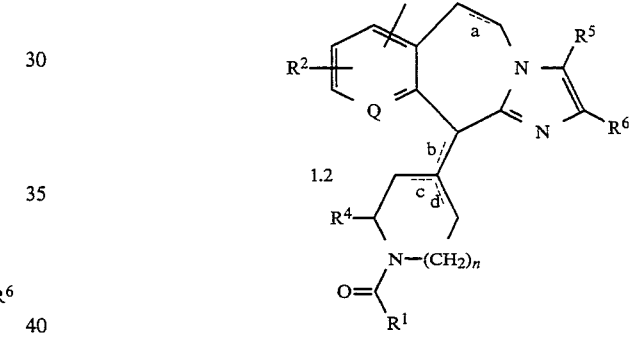

Suitable coupling reagents are carbodiimides, e.g., dicyclohexylcarbodiimide and 1-(3-dimethylaminopropyl)-3-ethylcarbodiimide, which may be combined with 1-hydroxybenzotdazole hydrate as a catalyst. A preferred reagent is 1-(3-dimethylaminopropyl)-3-ethylcarbodiimide, and a combination of this reagent with the aforementioned catalyst is preferred. The reaction is carded out at temperatures ranging from about $-25°$ C. to about $+50°$ C., and a preferred temperature is about $0°$ C. Exemplary of an organic carboxylic acid is $R^1CO_2H$ wherein $R^1$ is as described above. The solvent for the reaction is an organic solvent e.g., a chlorocarbon like carbon tetrachloride, chloroform, dichloromethane, ethylenedichloride and the like. A preferred solvent is dichloromethane.

Other methods for making compounds 1.2 from compounds 3.0 are well known to those skilled in the art; e.g., a reaction between compound 3.0 and the acid chloride, $R^1COCl$, corresponding to the acid $R^1CO_2H$ also leads to compounds 1.2.

(c) A compound (1.4) of formula 1.0, wherein Q is CH or N, is made by allowing a compound of formula 1.3, wherein Q is CH, N, 15 or N-O, to react with a deoxygenating reagent:

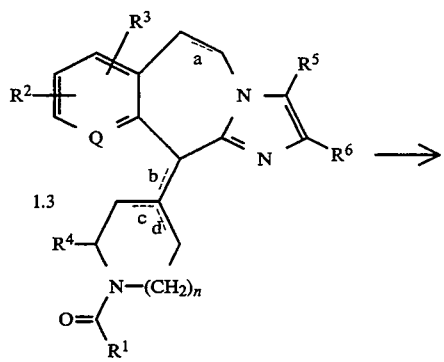

1.3

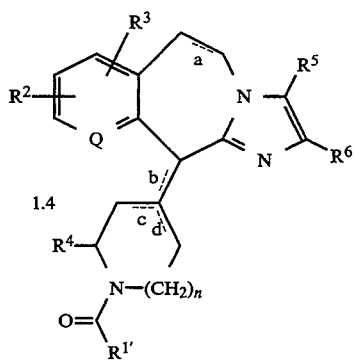

1.4 wherein R[1]' is R[1] with the proviso that N-oxides of nitrogen containing heteroaryl moieties are excluded.

Suitable deoxygenating reagents are hexamethyidisilane combined with tetrabutylammonium fluoride, butadiene sulfone, diphosphorous tetraiodide, sodium hypophosphite combined with palladium on carbon, and phosphorous trichloride. A preferred reagent is the last of these. The reaction is carded out at temperatures from about −15° C. to about +100° C., and a preferred temperature is about ++25° C. The reaction is preferably carded out in a solvent and suitable solvents are chlorocarbons, e.g., chloroform, carbon tetrachloride, dichloromethane, and ethylenedichloride, and the like. Dichloromethane is a preferred solvent.

(d) A compound (1.3) of formula 1.0, wherein Q is CH, N, or N-O, is made by allowing a compound of formula 1.4, wherein Q is CH, N, or N-O, and R[1]' is as described above, to react with a peroxidizing reagent:

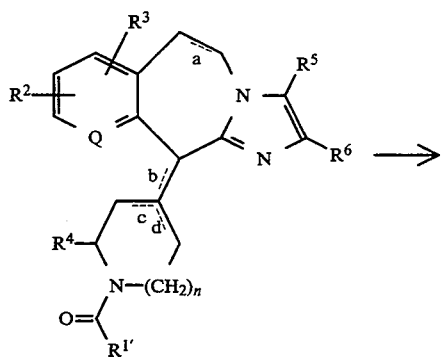

1.4

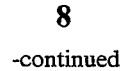

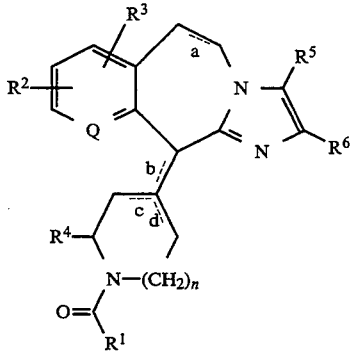

1.3

Suitable peroxidizing agents are monoperphthalic, 3-chlorobenzoic, peracetic acid, trifluoroperacetic acids, and the like. A preferred peroxidant is 3-chloroperbenzoic add. The reaction is carded out in a solvent, preferably a chlorocarbon like chloroform dichloromethane, or ethylenedichloride; and a preferred solvent is dichloromethane. The reaction temperature ranges from about −15° C. to about +25° C., and preferred temperature is 25° C. The reaction may also be carded out at elevated temperatures, preferably at the boiling point of the chosen solvent, in which instance a radical inhibitor is added to stabilize the peroxidant. A preferred inhibitor is 4,4'-thiobis-(6-tert.-butyl-3-methyl-phenol).

When Q is N, the above reaction is carded using a molar excess (preferably about 2:1) of a compound of formula 1.4 as compared to the peroxidizing agent. The reaction product under such conditions is a mixture of four compounds. One compound is the unchanged compound of formula 1.4. In another compound, Q has been converted to NO and

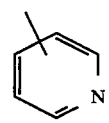

remains unchanged. In a third compound, Q has been converted to NO and

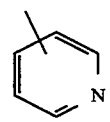

has been converted to the corresponding moiety

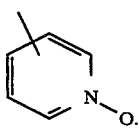

In the desired compound of formula 1.3, Q remains unchanged as N while is converted to the corresponding moiety

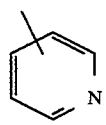

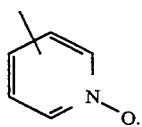

This desired product of formula 1.3 can be isolated by conventional separatory techniques.

In general, a reaction similar to the above reaction may be used to convert compounds of formula 1.0 wherein Q is CH, N or NO and $R^1$ is a nitrogen containing heteroaryl moiety excluding N-oxides, to the corresponding heteroaryl N-oxides thereof.

(e) A compound (1.6) of formula 1.0 is made by allowing a compound (1.2) wherein Q is CH, N, or NO to react with a sulfurating agent, e.g., Lawesson's reagent or $P_2S_5$:

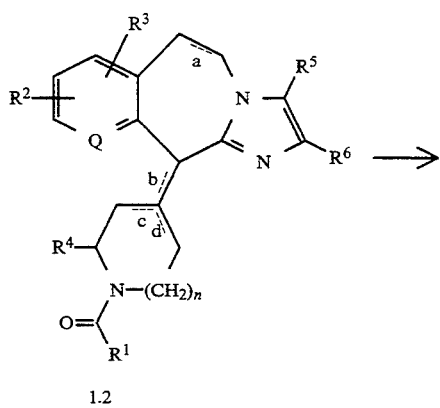

1.2

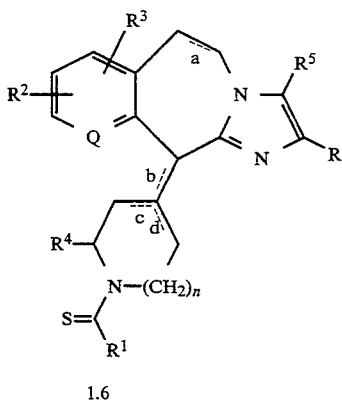

1.6

Methods for converting carbonyl compounds like 1.2 to thiocarbonyl compounds like 1.6 are well known to those skilled in the art.

Intermediate compounds 2.0–10.0 of this invention are known or could be prepared by known methods or are prepared by processes (f) through (i) below:

(f) An intermediate compound of formula 2.0, is prepared by allowing an intermediate compound of formula 5.0 to acylate an intermediate compound of formula 4.0.

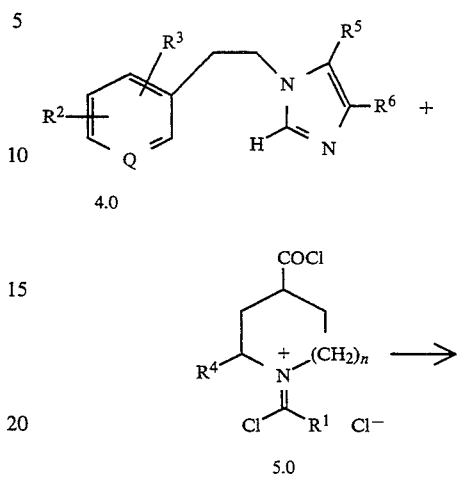

4.0

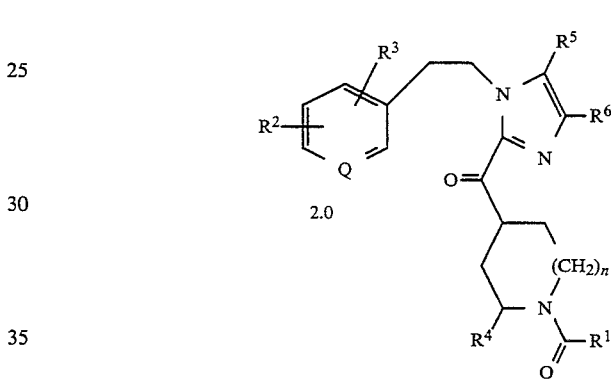

2.0

The acylation reaction is carried out in a solvent, and suitable solvents are chlorocarbons like chloroform, dichloromethane or ethylene dichloride and lower alkyl nitriles of which acetonitrile is preferred. The reaction takes place at temperatures ranging from about +25° C. to about +150° C., preferably at the boiling point of the solvent employed. Either one equivalent or an excess of intermediate compound 5.0 is employed, an excess of about two to four equivalents being preferred. Using one equivalent favors formation of intermediate compound 2.0, whereas an excess favors that of 6.0, which compound is defined in part (g) below. The reaction requires that a base be present, and suitable bases are tertiary amines, e.g., diisopropylethylamine, triethylamine, pyridine, 4-dimethylaminopyridine, and the like. A preferred base is triethylamine.

In some cases, the reaction of compounds 4.0 and 5.0 may also produce a compound of formula 6.0 below that is admixed with a compound of formula 2.0.

(g) An intermediate compound of formula 2.0 is also made by allowing an alkali metal hydroxide, such as sodium hydroxide or potassium hydroxide; or an alkali metal carbonate, such as sodium or potassium carbonate, or an aqueous acid, to hydrolyze an intermediate compound of formula 6.0:

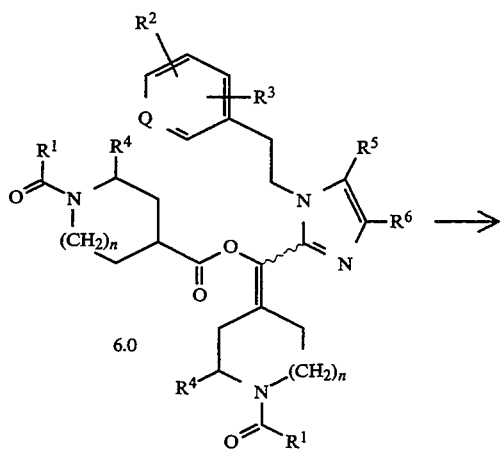

6.0

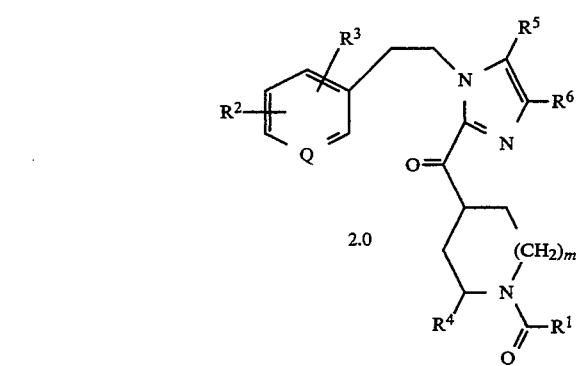

2.0

The hydrolysis reaction takes place in the presence of a base as described above or an acid. The aqueous acid may be an aqueous mineral acid, e.g., hydrochloric and sulfuric acids, and a preferred mineral acid is hydrochloric.

(h) A compound of formula 4.0 is made by allowing a compound of formula 7.0, wherein L is a leaving group, such as a halide like chloride, bromide, or iodide or an alkyl or aryl sulfonate, like such as -$OSO_2$-($C_1$-$C_7$ alkyl),-$SO_2$-($C_3$-$C_7$ cycloalkyl) or-$OSO_2$-aryl, to react with a compound of formula 8.0, in which $R^{11}$ is chosen from H, C(=O)-($C_1$-$C_7$ alkyl), (C=O)-($C_3$-$C_7$ cycloalkyl), C(=O)-aryl, C(=O)-heteroaryl, or an alkali metal:

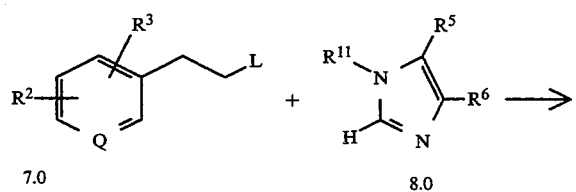

7.0    8.0

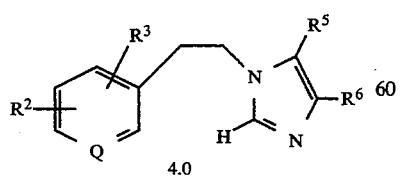

4.0

Preferred intermediate compounds for this alkylation are compounds 7,0 wherein L is bromine and 8.0 wherein $R^{11}$ is $CH_3CO$, Chem. Pharm. Bull. Japan (31, 1213-1221 (1983)) teaches preferred conditions of temperature, solvent, and time for carrying out the reaction when L is bromine and $R^{11}$ is $CH_3CO$.

Compounds of formula 7.0 are well known to one skilled in the art, and are commercially available, e.g., phenethyl bromide from the Aldrich Chemical Company, or are readily prepared by standard methods from commercially available compounds, e.g., 3-chlorophenethyl alcohol, also from the Aldrich Chemical Company. Compounds of formula 8.0 are known and are available commercially or can be prepared by known methods.

The reaction of an intermediate compound of formula 7.0 with an intermediate compound of formula 8.0 may also form an intermediate compound of formula 9.0 below.

(i) A compound of formula 4.0 also may be prepared by allowing a compound of formula 9.0 to react with an alkali or alkaline metal hydroxide or alkoxide, e.g., -O-($C_1$-$C_7$) alkyl, -O-($C_3$-$C_7$ cycloalkyl):

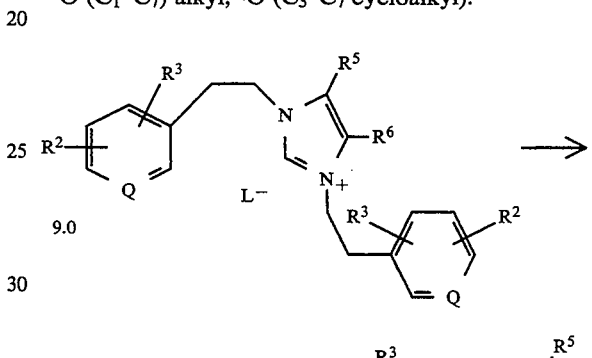

9.0

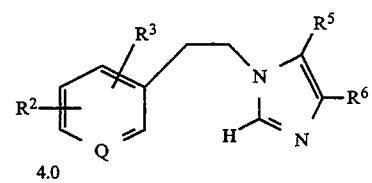

4.0

The reaction is carried out at temperatures ranging from +25° C. to +150° C., preferably at an elevated temperature, and namely at the boiling point of the solvent employed. The reaction is carded out in a solvent, and suitable solvents are lower alcohols, e.g., methanol, ethanol, tert.-butanol, and the like. A preferred solvent is ethanol. The reaction requires a base, and suitable bases are alkali metal lower-alkoxides. Suitable alkali metal cations are lithium, potassium, sodium, and cesium; while suitable lower alkoxides are methoxide, ethoxide, and tert.-butoxide. Preferred lower alcohol and alkali metal lower-alkoxide are respectively ethanol and potassium tert.-butoxide.

(j) A compound of formula 5.0 is made by allowing a compound of formula 10.0 to react with a reagent such as thionyl chloride, phosphorous oxychloride, phosphorous pentachloride, oxalyl chloride, phosgene, and the like:

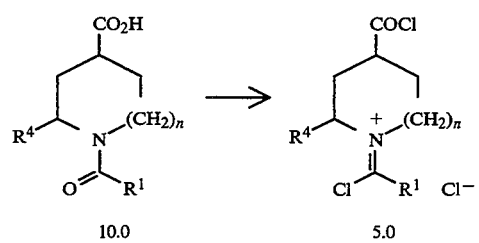

10.0    5.0

Methods of making acid chlorides, represented by compounds 5.0, and of making imminium chlorides, also represented by compounds 5.0 are well-known to those skilled in the art. Compounds of formula 10.0 are known or can be prepared in accordance with known methods.

The compounds of the invention may be administered in a conventional manner such as orally, rectally, or parenterally. Preferably, the compounds of the invention are administered orally.

For preparing pharmaceutical compositions from the compounds of formula 1.0 of the invention, inert, pharmaceutically acceptable carriers can be either solid or liquid. Solid form preparations include powders, tablets, dispersible granules, capsules, cachets, and suppositories.

A solid carder can be one or more substances which may also act as diluents, flavoring agents, solubilizers, lubricants, suspending agents, binders or tablet disintegrating agents; it can also be an encapsulating material.

In powders, the carrier is a finely divided solid which is in admixture with the finery divided active compound. In the tablet the active compound is mixed with carder having the necessary binding properties in suitable proportions and compacted in the shape and size desired. The powders and tablets preferably contain from 5 or 10 to about 70 percent of the active ingredient. Suitable solid carders are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carder providing a capsule in which the active component (with or without other carders) is surrounded by carrier, which is thus in association with it. Similarly, cachets are included. Tablets, powders, cachets and capsules can be used as solid dosage forms suitable for oral administration.

For preparing suppositories, a low melting wax such as mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be convened, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersions, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparations, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient. A typical recommended dosage is from about 0.01 mg/kg to 1000 mg/kg. preferably about 1 mg/kg to about 100 mg/kg, preferably orally.

The daily dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The compounds of formula 1.0 possess PAF antagonistic properties. These compounds are, therefore, useful when PAF is a factor in the disease or disorder. This includes allergic diseases such as asthma, adult respiratory distress syndrome, urticaria and inflammatory diseases such as rheumatoid arthritis and osteoarthritis. For example, PAF is an important mediator of such processes as platelet aggregation, smooth muscle contraction (especially in lung tissue), vascular permeability and neutrophil activation. Recent evidence implicates PAF as an underlying factor involved in airway hyperreactivity, shock, edema, hypersensitivity, disseminated loss of platelets by pregnant women, and in diseases associated with implantation of embryo in utero.

In particular, the compounds of formula 1.0 of the invention can be used to treat allergy and inflammatory caused diseases and their preferred use is for treating allergic chronic obstructive lung diseases. Chronic obstructive lung disease as used herein means disease conditions in which the passage of air through the lungs is obstructed or diminished such as is the case in asthma, bronchitis and the like.

Activity of compounds of formula 1.0 of the invention was demonstrated by the procedures set forth below.

A. PAF Antagonism Assay

In vitro Assay:

Platelet-activating factor (PAF) causes aggregation of platelets by a receptor-mediated mechanism. Therefore, PAF-induced platelet aggregation provides a simple and convenient assay to screen compounds for PAF antagonism.

Human blood (50 ml) was collected from healthy male donors in an anticoagulant solution (5 ml) containing sodium citrate (3.8%) and dextrose (2%). Blood was centrifuged at 110 $\times$g for 15 min. and the supernatant platelet-rich plasma (PRP) carefully transferred into a polypropylene tube. Platelet-poor-plasma (PPP) was prepared by centrifuging PRP at 12,000$\times$g for 2 min, in a Beckman Microfuge B. PRP was used within 3 hours of drawing the blood.

PAF was dissolved in chloroform:methanol (1:1, v/v) at a concentration of 2 mg/ml and stored at $-70$ C. An aliquot of this solution was transferred to a polypropylene tube and dried under a flow of nitrogen gas. To the dried sample was added Hepes-saline-BSA (BSA =bovine serum albumin) buffer (25 mM Hepes, pH 7.4, 1254 mM NaCl, 0.7 mM $MgCl_2$ and 0.1% BSA buffer) to obtain a 1 mM solution. The solution was sonicated for 5 min. in a bath sonicator. This stock solution was further diluted to appropriate concentrations in Hepes-saline-BSA buffer. Collagen (Sigma) and adenosine diphosphate (ADP)(Sigma) were purchased as solutions. Test compounds were initially dissolved in dimethyl sulfoxide (DMSO) at a concentration of 50 mM and then further diluted in Hepes-saline-BSA buffer to achieve appropriate concentrations. Hepes is an abbreviation for (N-[2-Hydroxyethyl]piperazine-N'-[2-ethanesulfonic acid]).

When an aggregating agent such as PAF is added to PRP, platelets aggregate. An aggregometer quantifies this aggregation by measuring and comparing light (infra-red) transmission through PPP and PRP. Aggregation assays were performed using a dual-channel aggregometer (Model 440, Chrono-Log Corp., Havertown, Pa.). PRP(0.45 ml) in aggregometer cuvettes was continually stirred (37 C). Solutions (50 microliters) of test compounds or vehicle were added to the PRP and, after incubation for 2 minutes, 10–15 $\mu$l aliquots of PAF solution were added so as to achieve a final PAF concentration of 10–15 $\times 10^{-8}$M. Incubations were continued until the increase in light transmission reached a maximum (usually 2 min.). This increase in light transmission reflecting platelet aggregation is transmitted to a computer by the Chrono-Log model 810 AGGRO/LINK interface(Supplied by the Chrono-Log Corp. Havertown, Pa.). The AGGRO/LINK calculates the slope of the transmission change, thus providing the rate of aggregation. Values for inhibition were calculated by comparing rates of aggregation obtained in the absence and the presence of the compound. For each experiment, a standard PAF antagonist such as 8-chloro-6,11-(1-acetyl-4-piperidylidene-5H-benzo[5,6-]cyclohepta[1,2-b]pyridine was used as a positive control.

Compounds that inhibit PAF-induced aggregation were tested against several other aggregating agents including collagen (0.2 mg/ml) and adenosine diphosphate(2 microMolar). Compounds showing no activity against these latter agents were considered to be specific PAF antagonists. Results are shown below.

The inhibitory concentration ($IC_{50}$) is the concentration of compound in micromoles per liter at which 50% of the aggregation is inhibited, as measured by the light transmission through each sample of PRP as compared to that through PPP.

By the above test the following $IC_{50}$ values were obtained:

$IC_{50}(\mu M)=5$ for 4-(5,6-dihydro-11H-imidazo[2,1-b][3]benzazepin-11-ylidene)-1-(4-pyridinylcarbonyl)-piperidine $N^1$-oxide.

$IC_{50}(\mu M)=35$ for 1-acetyl-4-(5,6-dihydro-11H-imidazo[2, 1-b][3]benzazepin-11-ylidene)-piperidine.

At a 50 $\mu$M dose, 4-(5,6-dihydro-11H-imidazo[2,1b][3]benzazepin-11-ylidene)-1-(4-pyridinylcarbonyl)-piperidine inhibited in vitro platelet aggregation by 17%.

The compounds of formula 1.0 of the invention may also be demonstrated to be active by the following in vivo PAF Antagonist Test.

B. PAF-Induced Bronchospasm in Guinea Pigs

In Vivo Assay

Non-sensitized guinea pigs are fasted overnight, and the following morning anesthetized with 0.9 ml/kg i.p. of dialurethane (0.1 g/ml of diallybarbituric acid, 0.4 g/ml of ethylurea and 0.4 g/ml of urethane). The trachea is cannulated and the animals are ventilated by a Harvard rodent respirator at 55 strokes/min. with a stroke volume of 4 ml. A side arm to the tracheal cannula is connected to a Harvard pressure transducer to obtain a continuous measure of intratracheal pressure, which is recorded on a Harvard polygraph. The jugular vein is cannulated for the administration of compounds. The animals are challenged i.v. with PAF (0.4 ug/kg in isotonic saline containing 0.25% bovine serum albumin(BSA)) and the peak increase in inflation pressure that occurred within 5 min. after challenge is recorded. Test compounds can be administered either orally (2 hrs. prior to PAF as a suspension in 0.4% methylcellulose vehicle) or intravenously (10 min. prior to PAF as a solution in dimethylsulfoxide).

The following examples are illustrative of the invention and are not intended to limit it. Temperatures are in degrees Celsius unless otherwise indicated.

EXAMPLE 1

A solution of phosphorous trichloride (0.25 ml)in dichloromethane (3 ml) was added to a solution of 4-(5,6-dihydro-11H-imidazo[2,1-b][3]benzazepin-11-ylidene)-1-(4-pyridinylcarbonyl)-piperidine $N^1$-oxide (B, 0.4 g) and dichloromethane (5 ml). The reaction mixture was allowed to stir overnight at 25° C. in an atmosphere of nitrogen, and was then poured onto a mixture of ice and water. The resulting mixture was basified with concentrated aqueous ammonia, and the aqueous layer was extracted with dichloromethane. The dried (magnesium sulfate), filtered extracts were concentrated to give 4-(5,6-dihydro-11H-imidazo[2,1-b][3]benzazepin-11-ylidene )-1-(4-pyridinylcarbonyl)-piperidine (A, 0.34 g), m.p. 207°–209° C. from carbon tetrachloride.

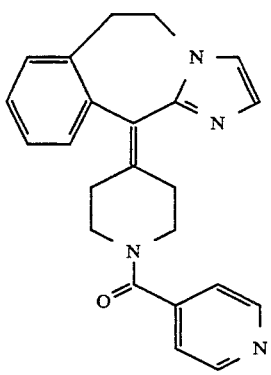

A 4-(5,6-dihydro-11H-imidazo[2,1-b][3]benzazepin-11-ylidene)-1-(4-pyridinylcarbonyl)-piperidine N¹-oxide (B) was prepared as described in Example 2.

EXAMPLE 2

1-(3-dimethylaminopropyl)-3-ethylcarbodiimide hydrochloride (0.61 g) was added to a solution of 6,11-dihydro-11-(4-piperidylidene)-5H-imidazo[2,1-b][3]benzazepine (C, 0.52 g), pyridine-4-carboxylic acid N-oxide (0.44 g) and 1-hydroxybenzotriazole hydrate (0.43 g)in dichloromethane (20 ml) at 0°–5° C. The reaction mixture was then allowed to stir and to warm to 25° C. overnight. Water and 1 M sodium bicarbonate solution were added, and the aqueous layer was extracted with dichloromethane. Combined organic extracts were washed sequentially with water and brine, and were dried, filtered, and concentrated to give 4-(5,6-dihydro-11H-imidazo[2,1-b][3]benzazepin-11-ylidene)-1-(4-pyridinylcarbonyl)-piperidine N¹-oxide (B, 0.54 g), m.p. 155°–159° C. from carbon tetrachloride-dichloromethane.

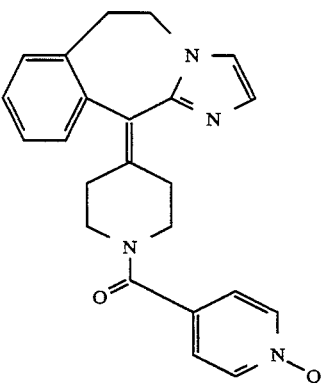

B 6,11-dihydro-11-(4-piperidinylidene)-5H-imidazo[2,1-b][3]benzazepine (C) was prepared as described in Example 4. The Aldrich Chemical Company supplies 1-(3-dimethylaminopropyl)-3-ethylcarbodiimide hydrochloride, pyridine-4-carboxylic acid N-oxide, and 1-hydroxybenzotriazole hydrate.

EXAMPLE 3

A solution of 1 -acetyl-4-[[1-(2-phenylethyl)-1H-imidazol-2yl]carbonyl]piperidine (D, 1.12 g) in trifluoromethanesulfonic acid (12 ml) was heated 18 hrs. at 60° C. under nitrogen. The solution was then cooled and poured over ice. The resulting mixture was neutralized with solid sodium bicarbonate, and the aqueous layer was extracted with dichloromethane. Combined extracts were sequentially washed with water and saturated aqueous sodium chloride solution. The dried and filtered organic solution was then concentrated to give an oil which crystallized from ether to afford 1-acetyl-4-(5,6-dihydro-11H-imidazo[1,2-b][3]benzazepine-11-ylidene)-piperidine (E, 0.83 g); FAB-MS: m/z 308 (100%, [C₁₉H₂₁N₃O+H]⁺).

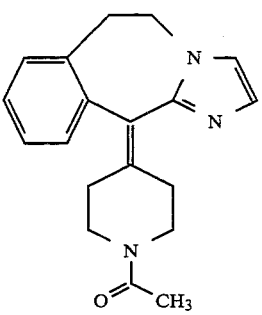

E 1-acetyl-4-[[1-(2-phenylethyl)-1H-imidazol-2-yl]carbonyl]piperidine (D) was prepared as follows.

To a stirred, cooled (0°–5° C.) solution of 1-(2-phenylethyl)-1H-imidazole (F, 3.00 g) and triethylamine (19.5 ml) in acetonitrile (75 ml) was added 4-(chlorocarbonyl)-1-(1-chloroethylidene)piperidinium chloride (G, 7.29 g). The resulting mixture was allowed to warm to 10° C. and was stirred 3 hrs. It was diluted with water and was saturated with sodium bicarbonate. The mixture was extracted with dichloromethane. Combined extracts were washed sequentially with water and saturated aqueous sodium chloride solution. The dried and filtered extracts were concentrated to give an oil (6.40 g) which crystallized to afford 1-acetyl-4-[[1-(2-phenylethyl)-1H-imidazol-2-yl]carbonyl]piperidine (D, 1.45 g), m.p. 113°–116° C. from ethyl acetate.

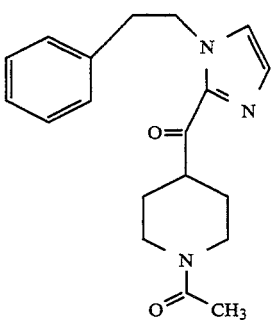

D

The mother liquor remaining after crystallization of 1-acetyl-4-[[1-(2-phenylethyl)-1H-imidazol-2-yl]carbonyl]piperidine (D) was chromatographed over silica gel. Dichloromethane-methanol-concentrated aqueous ammonia (97.5-2.25-0.25) eluted (1-acetyl-4-piperidylidene)[1-(2-phenylethyl)-1H-imidazol-2-yl]methyl 1-acetyl-4-piperidine carboxylate (H) as an oil; MS: m/z 478 (10%, M⁺).

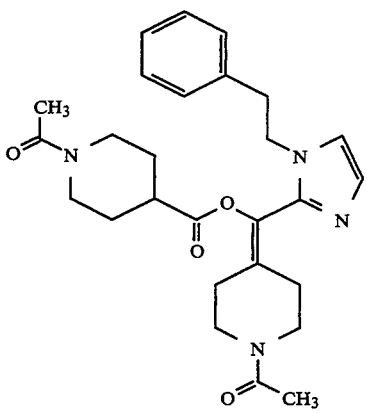

H 1-(2-phenylethyl)-1H-imidazole (F) and 4-(chlorocarbonyl)-1-(1 chloroethylidene)piperidinium chloride (G) were prepared as follows.

A stirred mixture of 1,3-bis(2-phenylethyl)-1H-imidazolium iodide (J, 16.5 g), potassium tert.-butoxide (9.16 g), and ethanol(165 ml) was refluxed 68 hrs. under nitrogen. The mixture was cooled to 25° C., diluted with water, and concentrated to remove ethanol. The residue was partitioned between dichloromethane and water. Combined organic extracts were dried, filtered, and concentrated to give 1-(2-phenyl)-1H-ethyl-]imidazole (F, 6.24 g), distilling at 200 ° C. (oven temperature) at 0,25 mm of mercury.

Chem. Pharm. Bull. Japan (31, 1213-1221 (1983)) teaches another method for making 1-(2-phenylethyl)-1H-imidazole F.

Thionyl chloride (60 ml) was added slowly to a stirred solution of 1-acetyl-4-piperidinecarboxylic acid (I, 25.0 g) in dichloromethane (250 ml) at 25° C. The mixture was allowed to stir 2 hrs. and was then diluted with petroleum ether (35°-65° C., 250 ml) to precipitate 4-(chlorocarbonyl)-1-(1-chloroethylidene )piperidinium chloride (G, 34 g) as a colorless solid, which was used directly in the next step.

1,3-bis(2-phenylethyl)-1H-imidazolium iodide (J) was prepared as follows.

A solution of (2-bromoethyl)benzene (27.3 ml), sodium iodide (60.0 g), 1-acetylimidazole (22.2 g), and acetonitrile (220 ml) was refluxed 6.5 hrs. under nitrogen. The solution was cooled to 25° C. and the acetonitrile was evaporated. Water and potassium carbonate were added to the oily residue, which was extracted with dichloromethane. Combined extracts were washed with water, dried, filtered, and concentrated to give 1,3-bis(2-phenylethyl)-1H-imidazolium iodide (J, 35.4 g), m.p. 145.5°-147° C. from ethyl acetate.

The Aldrich Chemical Company supplied (2-bromoethyl)benzene and 1-acetylimidazole.

EXAMPLE 4

A solution of 1-acetyl-4-(5,6-dihydro-11H-imidazo[1,2-b][3]benzazepine-11-ylidene)-piperidine (E, 3.7 g) concentrated hydrochloric acid (100 ml), and water (100 ml) was refluxed for 20 hrs. The solution was cooled and concentrated, and the residue was dissolved in water. The resulting solution was washed with ethyl acetate, and was then basified with 50% sodium hydroxide solution. The basic aqueous solution was extracted with dichloromethane, and combined extracts were washed with water. The dichloromethane solution was dried, filtered, and concentrated to give 6,11-dihydro-11-(4-piperidylidene)-5H-imidazo[2,1-b][3]benzazepine (C, 2.95 g), m.p. 287°-289° C. from dichloromethane-methanol.

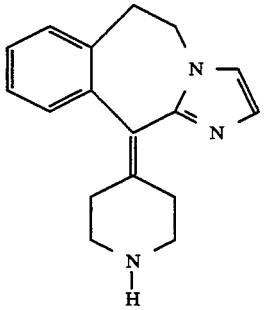

C 6,11-dihydro-11-(4-piperidinylidene)-5H-imidazo[2,1-b][3]benzazepine (C) was also prepared as follows.

A mixture (3.87 g) of 1-acetyl-4-[[1-(2-phenylethyl)-1H-imidazol-2yl]carbonyl]piperidine (D), (1-acetyl-4-pipendinylidene)[1-(2-phenylethyl)-1H-imidazol-2-yl]methyl 1 -acetyl-4-piperidine carboxylate (H), and 6 N hydrochloric acid (100 ml) was refluxed for 20 hrs. The cooled reaction mixture was concentrated, and the residue was diluted with water. The resulting mixture was sequentially washed with ether and ethyl acetate. The acidic aqueous layer was basified with sodium hydroxide solution and was extracted with dichloromethane. The combined extracts were washed with water, dried, filtered, and concentrated to give [1-(2-phenyethyl)-1H-imidazol-2-yl](4-piperidinyl) methanone (K, 0.91 g), m.p. 230°-232° C. from dichloromethane-hexanes.

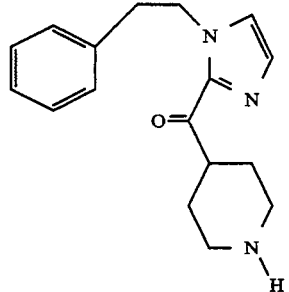

K

A solution of [1 -(2-phenyethyl)-1H-imidazol-2-yl](4-piperidinyl)methanone (K, 0.54 g) and trifluoromethanesulfonic acid (6.25 ml) was heated 18 hrs. at 60° C. The solution was then poured over a mixture of ice and water. The resulting mixture was extracted with dichloromethane, and combined extracts were washed with 1 M sodium bicarbonate solution. The dichloromethane solution was dried, filtered, concentrated, and chromatographed over silica gel. Dichloromethane-methanol-concentrated aqueous ammonia (95:4.5:0.5) eluted 6,11-dihydro-11-(4-piperidinylidene)-5H-imidazo[2,1 -b][3]benzazepine (C, 0.34 g), MS: m/z 265 (75, M+).

The following is an example of a pharmaceutical dosage form which contains a compound of the invention. As used herein, the term "active compound" is used to designate the compound 4-(5,6-dihydro-11H-imidazo[2.1-b][3]benzazepin-11-ylidene)-1-(4-pyridinylcarbonyl)-piperidine $N^1$-oxide. The scope of the invention in its pharmaceutical composition aspect is not to be limited by the example provided since any other compound of formula 1.0 can be substituted into the pharmaceutical composition example.

Example 5 (Tablets)

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|   | Total | 300 | 700 |

Method of Manufacture

Mix Item Nos. 1 and 2 in a suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weigh on a suitable tablet machine.

In the above example, the active compound may be any compound of the invention, such as 4-(5,6-dihydro-11H-imidazo[2,1-b][3]benzazepin-11-ylidene)-1-(4-pyridinylcarbonyl)-piperidine $N^1$-oxide While the present invention has been described in conjunction with the specific embodiments set forth above, many modifications, alternatives, and variations thereof will be apparent to those of ordinary skill in the art. All such modifications, alternatives, and variations are intended to fall within the spirit and scope of the present invention.

We claim:

1. A compound of the formula

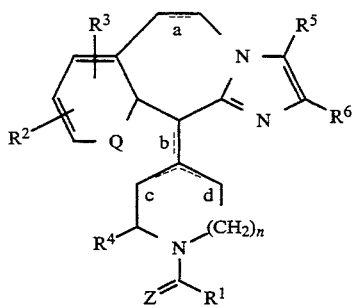

1.0 wherein $R^1$ is H, $C_1$-$C_7$ alkyl, $C_3$-$C_7$ cycloalkyl, $CF_3$, aryl having from 6 to 14 carbon atoms, substituted aryl, heteroaryl having at least one O, S and/or N interrupting a carbocyclic ring structure with the aromatic heterocyclic group having from 2 to 14 carbon atoms, -O-$C_1$-$C_7$ alkyl, or -O-$C_3$-$C_7$ cycloalkyl; $R^2$ and $R^3$ are each independently H, $C_1$-$C_7$ alkyl, $C_3$-$C_7$ cycloalkyl, $CF_3$, $NO^2$, halogen, $OR^7$, $NR^8R^9$ or $S(O)_mR^{10}$, wherein m is 0, 1 or 2; $R^4$ is H, $C_1$-$C_7$ alkyl, arylmethyl with the aryl portion having from 6 to 14 carbon atoms, or substituted arylmethyl; $R^5$ and $R^6$ are each independently H, $C_1$-$C_7$ alkyl, $C_3$-$C_7$ cycloalkyl, aryl having from 6 to 14 carbon atoms, substituted aryl, heteroaryl having at least one O, S and/or N interrupting a carbocyclic ring structure with the aromatic heterocyclic group having from 2 to 14 carbon atoms, arylmethyl with the aryl portion having from 6 to 14 carbon atoms, or substituted arylmethyl; $R^7$, $R^8$ and $R^9$ are each independently H, $C_1$-$C_7$ alkyl, -C(=O)-($C_1$-$C_7$ alkyl), -C(=O)- aryl having from 6 to 14 carbon atoms, or -(C=O)heteroaryl having at least one O, S and/or N interrupting a carbocyclic ring structure with the aromatic heterocyclic group having from 2 to 14 carbon atoms; $R^{10}$ is $C_1$-$C_7$ alkyl, $C_3$-$C_7$ cycloalkyl, aryl having from 6 to 14 carbon atoms, substituted aryl, heteroaryl having at least one O, S and/or N interrupting a carbocyclic ring structure with the aromatic heterocyclic group having from 2 to 14 carbon atoms, substituted heteroaryl, arylmethyl with the aryl portion having from 6 to 14 carbon atoms, or substituted arylmethyl; one and only one of the dotted lines, a, b, c, and d, represents a carbon-carbon bond; n is 0, 1, 2 or 3; Z is O or S, Q is CH or a pharmaceutically acceptable acid addition, salt thereof.

2. A compound of claim 1 further characterized by one and only one of the dotted lines a and b representing a carbon-carbon bond.

3. A compound of claim 2 further characterized by the dotted line b representing a carbon-carbon bond; $R^1$ representing H, $C_1$-$C_7$ alkyl or heteroaryl; $R^2$ representing H or halogen; $R^3$ representing H or halogen; $R^4$ representing H; $R^5$ and $R^6$ each representing H; and n representing 1.

4. A compound of claim 3 further characterized by Z representing O, and $R^3$ representing H.

5. A compound of claim 4 further characterized by $R^1$ representing

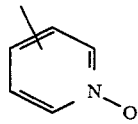

and $R^2$ representing H or chlorine meta to the Q position.

6. The compound of claim 5 further characterized by having the formula

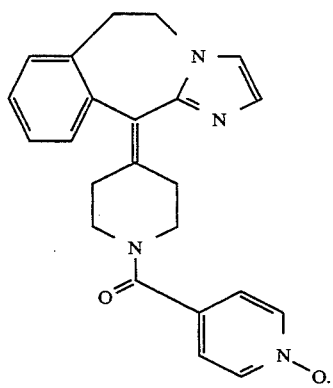

B

7. A compound of claim 4 further characterized by $R^1$ representing

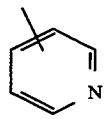

and R² representing H or chlorine meta to the Q position.

8. The compound of claim 7 further characterized by having the formula

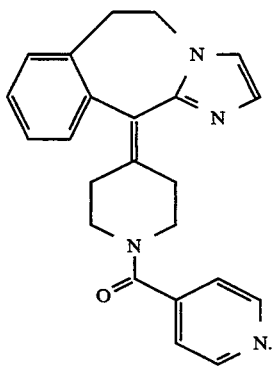

A

9. A compound of claim 4 further characterized by R¹ representing $C_1$-$C_7$ alkyl, and R² representing H or chlorine meta to the Q position.

10. The compound of claim 9 further characterized by having the formula

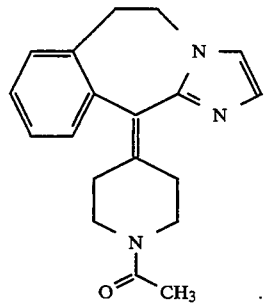

E

11. The compound of claim 3 further characterized by having the formula

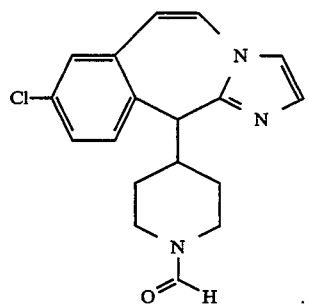

12. A pharmaceutical composition for use in treating allergic reactions or inflammation comprising an antiallergically effective amount or an anti-inflammatory effective amount of a compound of the formula 1.0 of claim 1, and an inert pharmaceutical carrier material.

13. A method for treating allergic diseases which comprises administering to a host in need of such treatment an antiallergically effective amount of a compound defined in claim 1.

14. A method for treating inflammation which comprises administering to a host in need of such treatment an effective amount of a compound defined in claim 1.

* * * * *